United States Patent
May et al.

(10) Patent No.: US 10,864,089 B2
(45) Date of Patent: Dec. 15, 2020

(54) SPINAL IMPLANT SYSTEM AND METHOD (71) Applicant: Warsaw Orthopedic, Inc, Warsaw, IN (US)

(72) Inventors: Jason M. May, Collierville, TN (US); Rodney Ray Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 220 days.

(21) Appl. No.: 15/726,257

(22) Filed: Oct. 5, 2017

(65) Prior Publication Data

US 2019/0105178 A1    Apr. 11, 2019

(51) Int. Cl.
*A61F 2/46* (2006.01)
*A61B 17/70* (2006.01)
*A61F 2/44* (2006.01)
*A61F 2/28* (2006.01)

(52) U.S. Cl.
CPC ........ *A61F 2/4611* (2013.01); *A61B 17/7041* (2013.01); *A61B 17/7076* (2013.01); *A61F 2/4455* (2013.01); *A61B 17/7032* (2013.01); *A61F 2002/2835* (2013.01); *A61F 2220/0025* (2013.01)

(58) Field of Classification Search
CPC ............ A61B 17/7076; A61B 17/7082; A61B 17/8875; A61F 2/4611
See application file for complete search history.

(56) References Cited

U.S. PATENT DOCUMENTS

| | | | | |
|---|---|---|---|---|
| 7,147,641 B2* | 12/2006 | Chen | ................. | A61B 17/068 606/104 |
| 9,332,983 B2* | 5/2016 | Shipp | ................. | A61B 17/064 |
| 10,548,642 B2* | 2/2020 | Harper | ............... | A61B 17/8875 |
| 2004/0243139 A1* | 12/2004 | Lewis | .................. | A61B 17/862 606/104 |
| 2005/0149031 A1* | 7/2005 | Ciccone | ............ | A61B 17/1615 606/280 |
| 2007/0276403 A1* | 11/2007 | Franks | ............... | A61B 17/7091 606/104 |
| 2008/0255576 A1* | 10/2008 | Protopsaltis | ....... | A61B 17/7091 606/104 |
| 2013/0296888 A1* | 11/2013 | Harper | .................. | A61B 17/58 606/139 |

* cited by examiner

*Primary Examiner* — David W Bates
(74) *Attorney, Agent, or Firm* — Sorell, Lenna & Schmidt, LLP (57) ABSTRACT

A surgical instrument comprises a first member defining a cavity configured for disposal of a plurality of implants and including a distal portion that retains the implants with the first member. An element is configured to urge the implants in a first, release direction and the first member having at least one tab movable to prevent movement of at least one of the implants in a second direction. A second member is engageable with the at least one tab. Systems, spinal implants and methods are disclosed.

20 Claims, 11 Drawing Sheets

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument comprises a first member defining a cavity configured for disposal of a plurality of implants and including a distal portion that retains the implants with the first member. An element is configured to urge the implants in a first, release direction and the first member having at least one tab movable to prevent movement of at least one of the implants in a second direction. A second member is engageable with the at least one tab. In some embodiments, systems, spinal implants, spinal constructs and methods are disclosed.

In one embodiment, the surgical instrument includes an inner tubular sleeve defining a cavity configured for disposal of a plurality of bone fastener receivers and including an expandable collet. The inner sleeve includes a piston engageable with the receivers in a first, release direction and a wall that defines at least one tab. An outer tubular sleeve is movable relative to the inner sleeve between a proximal position and a distal position such that the outer sleeve engages the at least one tab to prevent movement of at least one receiver in a second direction.

In one embodiment, a spinal implant system is provided. The spinal implant system comprises a surgical instrument including an inner sleeve configured for disposal of a plurality of bone fastener receivers and including an expandable collet. The inner sleeve includes a piston engageable with the receivers in a first, release direction and a wall that defines at least one tab. The surgical instrument includes an outer tubular sleeve engageable with the at least one tab to prevent movement of at least one receiver in a second direction. The at least one receiver is disposed with the collet. At least one bone fastener shaft is engageable with vertebral tissue and connectable with the at least one receiver.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument that comprises an implant dispenser. In some embodiments, the present surgical system includes a dispenser that retains one or more implants, such as, for example, implant receivers for attachment to another implant, such as, for example, screw shafts. In some embodiments, the implant dispenser is configured to retain and attach a tulip head receiver to a bone screw shaft. In some embodiments, the dispenser is spring loaded such that a plurality of implants are retained in a stacked configuration within the dispenser. In some embodiments, the implants are retained by a force applied by a compression spring. In some embodiments, the implants are retained by a collet. In some embodiments, the collet is disposed at a distal end of the dispenser. In some embodiments, the collet is flexible. In some embodiments, a force required to disengage the implant from the collet is higher than the compressive force applied by the implant compression spring. In some embodiments, the dispenser includes a spring tab to resist and/or prevent translation of the implant in a direction opposite to ejection of the implant. In some embodiments, the spring tab includes a retaining surface.

In some embodiments, the dispenser includes an outer sleeve. In some embodiments, the outer sleeve is configured to resist and/or prevent expansion of the spring tabs. In some embodiments, as one implant is ejected from the surgical instrument, a following implant in the stack of implants is urged and/or guided along the spring tab and loaded into the collet, such that the following implant is ready for attachment to a screw shaft.

In some embodiments, the present surgical system includes an implant dispenser that is configured to retain and attach a plurality of implants without the need to reload the dispenser or change instruments. In some embodiments, the implant dispenser is utilized with modular pedicle screws such that multiple implant receivers can be attached without requiring an instrument to be refilled at the back table. In some embodiments, the implant dispenser is configured to retain four implant receivers, corresponding to a one level posterior case. In some embodiments, the implant dispenser may be configured to retain an increased number of implants for procedures including multiple spinal levels. In some embodiments, the implant dispenser facilitates implant attachment and provides for fewer steps in procedures utilizing modular screws.

In some embodiments, the implant dispenser includes a handle. In some embodiments, the implant dispenser includes an outer sleeve. In some embodiments, the handle is connected with an outer sleeve compression spring by retaining pins. In some embodiments, the implant dispenser includes a spring guide disposed with the outer sleeve compression spring. In some embodiments, the implant dispenser includes an implant compression spring. In some embodiments, the implant dispenser includes a piston. In some embodiments, the implant dispenser includes an inner sleeve. In some embodiments, the inner sleeve includes a collet disposed at a distal end. In some embodiments, the collet is configured with an implant release force. In some embodiments, the inner sleeve includes spring tabs. In some embodiments, the spring tabs are configured to allow unidirectional translation of the implants relative to the inner sleeve. In some embodiments, a force is required to translate the implant relative to the release tabs and eject the implant.

In some embodiments, the outer sleeve is moveable relative to the inner sleeve between a proximal, open position to a distal, closed position. In some embodiments, in the open position, the spring tabs are exposed allowing the implant to translate into an eject position. In some embodiments, the handle is actuated such that a force applied to the handle expands the outer sleeve compression spring. In some embodiments, the force required to expand the collet is 9 pounds (lbs). In some embodiments, the force required to deflect the spring tabs to facilitate loading of a next implant is 1.5 lbs. In some embodiments, the implant compression spring applies a force of approximately 3-6 lbs to the implants. In some embodiments, the outer sleeve compression spring requires a force of 6 lbs to expand. In some embodiments, the force to expand the collet is less than an implant disconnection force prior to locking. In some embodiments, the force to expand the collet is greater than the force applied to actuate the handle to facilitate translation of the outer sleeve into the open position. In some embodiments, the force applied by the implant compression spring is greater than the force to expand the spring tabs to facilitate loading of the implant into the collet. In some embodiments, the force applied by the implant compression spring is less than the force to expand the collet to resist and/or prevent the implant compression spring from pushing the implants out of the dispenser.

In some embodiments, the collet includes a retaining surface configured to facilitate retaining the implant therein. In some embodiments, the spring tab includes a retaining surface. In some embodiments, the retaining surface of the spring tab is configured to resist and/or prevent translation of the implant back into the inner sleeve. In some embodiments, this configuration facilitates attachment of the implant with the screw shaft. In some embodiments, the outer sleeve is configured to prevent the spring tab from expanding.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-10, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or one or more spinal implants, such as, for example, one or more components of a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 10 includes a surgical instrument, such as, for example, an implant dispenser 12. Implant dispenser 12 can be employed to retain a plurality of implants such as, for example, bone fastener receivers 100 for connection with one or more bone fastener screw shafts 150, as described herein. In some embodiments, implant dispenser 12 can support and retain one or a plurality of bone fastener receivers 100 for delivery and/or introduction at a surgical site, as described herein. In some embodiments, implant dispenser 12 can support and retain one or a plurality of components of a bone fastener, alternate components of a bone fastener or implants. In some embodiments, implant dispenser 12 can support and retain components of various implants, such as, for example, interbody devices, interbody cages, bone fasteners, spinal rods, tethers, connectors, plates and/or bone graft. In some embodiments, one or more components of implant dispenser 12 comprise a magazine configured for holding a supply of implants that are fed automatically to the collet and released from implant dispenser 12.

Figure 8:
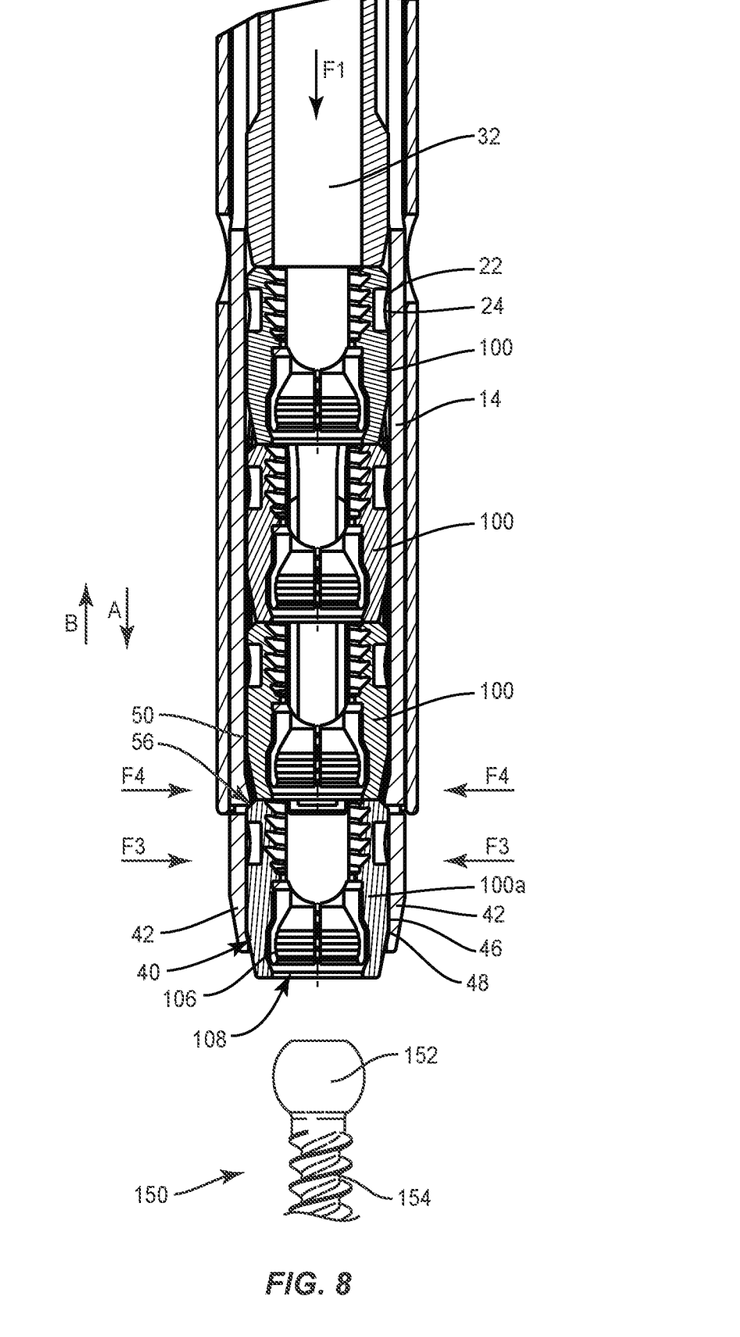
FIG. 8 is a break away cross section view of components of one embodiment of a surgical system in accordance with the principles of the present disclosure.

Implant dispenser 12 includes a member, such as, for example, an inner tubular sleeve 14. Implant dispenser 12 defines a longitudinal axis a. Inner sleeve 14 extends between a proximal portion 18 and a distal portion 20 along axis a. In some embodiments, inner sleeve 14 may have various configurations, for example, round, oval, polygonal, irregular, consistent, variable, uniform and non-uniform. Inner sleeve 14 includes an inner surface 22 that defines a cavity 24. Cavity 24 is configured for disposal of one or a plurality of receivers 100, as shown in FIG. 8.

Receivers 100 are stacked in a serial orientation within cavity 24 to facilitate loading, storage and/or ejection of receivers 100 from implant dispenser 12. Receivers 100 include a distal receiver, such as, for example, an ejection ready receiver 100a and one or more receivers 100 stacked proximally relative to receiver 100a. In some embodiments, receivers 100 include distal receiver 100a and three receivers 100 stacked proximal to receiver 100a. Receiver 100a is disposed within a collet 40, as described herein. Receiver 100a is attachable with screw shaft 150 and the next proximally disposed receiver 100 translates into an ejection position, as described herein. In some embodiments, implant dispenser 12 is configured to retain four implant receivers 100, corresponding to a one vertebral level posterior case.

Implant dispenser 12 includes an element 28 disposed with inner sleeve 14. Element 28 is configured to urge receivers 100 in a first, release direction, as described herein. Element 28 includes a piston 30 and a biasing member, such as, for example, a coil spring 32. Piston 30 is configured for moveable disposal within inner sleeve 14 and driven or urged in the direction, as shown by arrow A in FIG. 8, under the bias force of spring 32 to facilitate translation and/or release of receivers 100, as described herein. Piston 30 and spring 32 are contained within inner sleeve 14. Spring 32 causes piston 30 to provide a constant pressure to receivers 100 for guidance and translation within inner sleeve 14. A resistance force applied by tabs 50, as described herein, is configured to retain receivers 100 within cavity 24 prior to translation into the ejection position, as described herein. In some embodiments, piston 30 includes a T-shaped cross section. In some embodiments, the biasing member may include an elastomeric member, clip, leaf spring, gravity induced configuration, pneumatic configuration, hydraulic configuration and/or manual lever. A spring guide 34 is disposed with inner sleeve 14 and spring 32 to facilitate positioning and expansion of spring 32.

Spring 32 applies a force F1 to piston 30 to urge receivers 100 into distal portion 18 of inner sleeve 14 such that receiver 100a is disposed in the ejection position. In some embodiments, force F1 is in a range of approximately 3 to 6 lbs. In some embodiments, force F1 may vary depending on the number of receivers 100 disposed within cavity 24.

Inner sleeve 14 includes tabs 50 that are movable to resist and/or prevent axial translation of receivers 100 in a second direction, as shown by arrow B in FIG. 8, which facilitates attachment of a receiver 100 to a screw shaft 150, as described herein. Tabs 50 are disposed in alignment with a wall 54 of inner sleeve 14. Tabs 50 are biased outwardly relative to wall 54. Tabs 50 include a surface 56 configured to engage a proximal surface of ejection receiver 100a to resist and/or prevent axial translation of receivers 100, in the direction shown by arrow B in FIG. 8. In some embodiments, tabs 50 are configured as cantilever arms that extend along a portion of inner sleeve 14.

Figure 6:
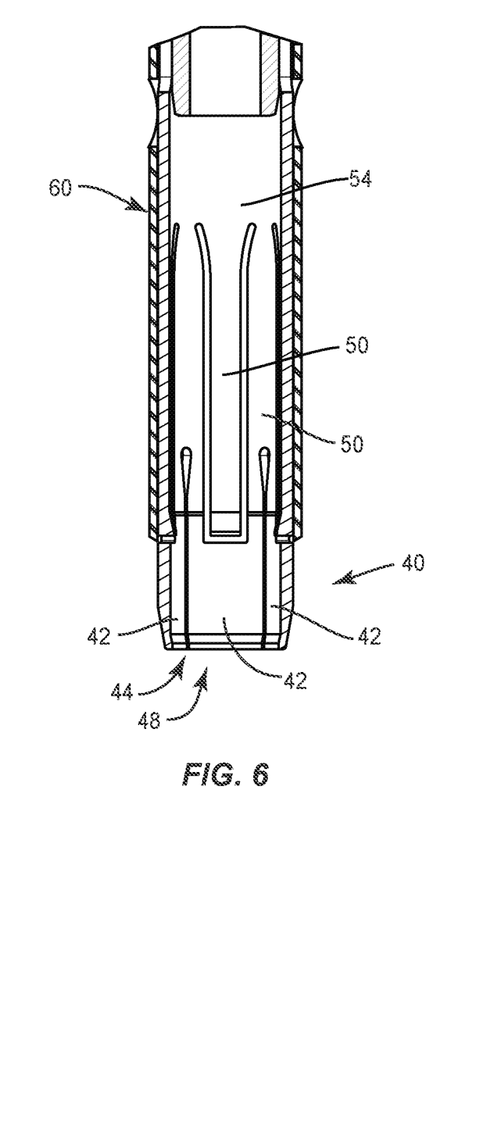
FIG. 6 is a break away view of the components shown in FIG. 5.

A member, such as, for example, an outer sleeve 60 translates relative to inner sleeve 14 to a closed position, as described herein and shown in FIG. 6, to deflect tabs 50 inwardly into engagement with the proximal surface of receiver 100a. Engagement of tabs 50 creates an interference fit between surface 56 and the proximal surface of receiver 100a. Surface 56 applies a force F4 to the proximal surface of receiver 100a to resist and/or prevent translation of receiver 100a, in the direction shown by arrow B, opposite to the direction shown by arrow A. Tabs 50 are configured to resist and/or prevent translation of receiver 100a into inner sleeve 14 prior to ejection of receiver 100a, as described herein. Upon ejection of receiver 100a from collet 40 and disposal of outer sleeve 60 in an open position, as described herein and shown in FIG. 7, force F4 is applied to a distal surface of the next proximally disposed receiver 100 oriented for disposal with collet 40. Force F1 of spring 32 overcomes force F4 applied to the distal surface of the next proximally disposed receiver 100 to deflect tabs 50 outwardly to facilitate loading of the next receiver 100 into collet 40. In some embodiments, force F4 is approximately 1.5 lbs.

Figure 5:
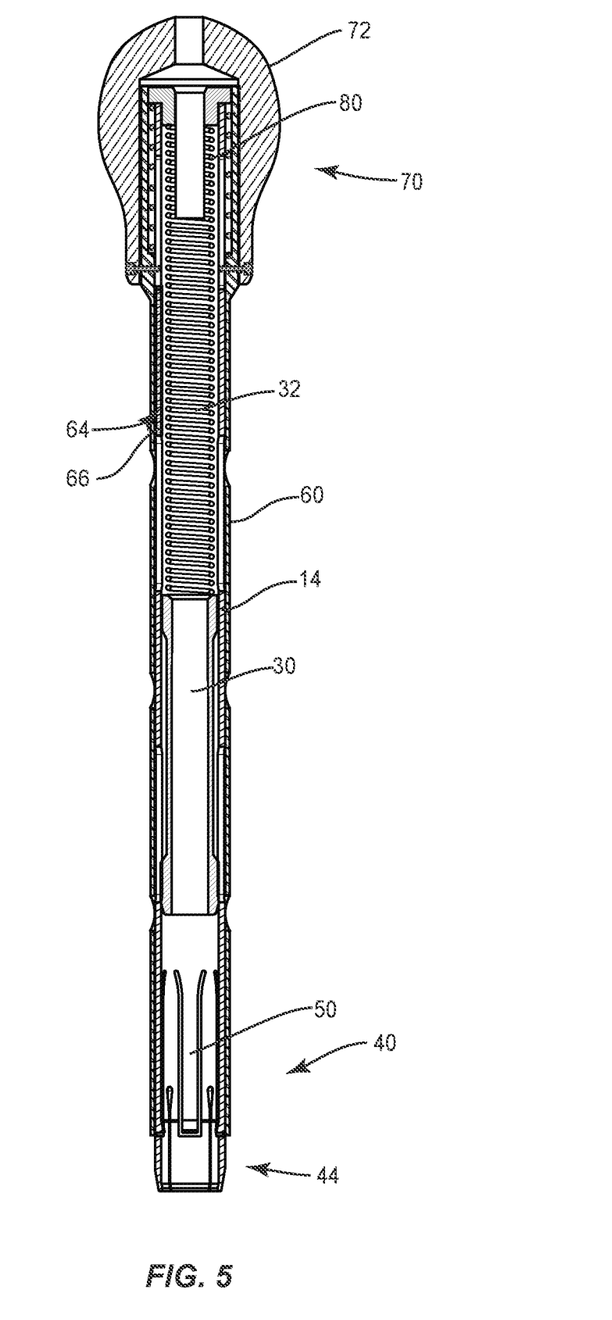
FIG. 5 is a cross section view of the components shown in FIG. 1.
Figure 7:
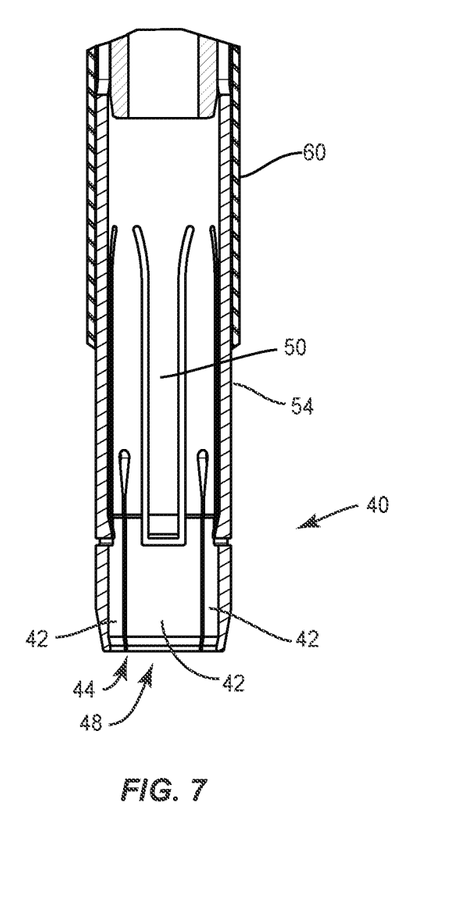
FIG. 7 is a break away view of the components shown in FIG. 5.

Collet 40 is disposed at a distal end of inner sleeve 14, as shown in FIGS. 5-7. Collet 40 extends from portion 20 and is configured for engagement with one or more receivers 100 for movement between an expanded configuration and a contracted configuration. Collet 40 includes a plurality of cantilevered fingers 42 extending in a tapered configuration. Fingers 42 are circumferentially disposed and are equidistantly spaced apart. Fingers 42 are spaced apart by a gap 44 defined by opposite planar sidewalls. Fingers 42 include an inner surface 46 defining a chamber 48. Chamber 48 is co-axial with axis a. Chamber 48 has a cylindrical cross-section and is configured for disposal of receiver 100a. In some embodiments, chamber 48 may have various cross section configurations, such as, for example, oval, oblong, triangular, rectangular, square, polygonal, irregular, uniform, non-uniform, variable, tubular and/or tapered.

Collet 40 is expandable from the contracted configuration such that a receiver 100 engages fingers 42 to expand collet 40 for loading the next proximally disposed receiver 100 into chamber 48. In the expanded configuration of collet 40, fingers 42 are inwardly biased to the contracted configuration such that collet 40 retains receiver 100a within chamber 48. In the contracted configuration, surface 46 applies a force F3 to receiver 100a to retain receiver 100a within chamber 48. Force F3 is greater than force F1 to retain receivers 100 with implant dispenser 12 and prevent spring 32 from undesirably driving and/or releasing receivers 100. In some embodiments, force F3 is overcome by drawing collet 40 off of a receiver 100a connected with a screw shaft 150 with a force greater than force F3, which may include the connecting force of receiver 100a/screw shaft 150 and/or fixation of screw shaft 150 with tissue. As such, receiver 100a is releasable from collet 40 and a next receiver 100 translates into chamber 48 into the ejection position, similar to receiver 100a. In some embodiments, force F3 is approximately 9 lbs.

Outer sleeve 60 extends between a proximal end 62 and a distal end 64. Outer sleeve 60 extends along longitudinal axis a. In some embodiments, outer sleeve 60 may have various configurations, for example, round, oval, polygonal, irregular, consistent, variable, uniform and non-uniform. Outer sleeve 60 includes an inner surface 64 that defines a cavity 66. Cavity 66 is configured for disposal of inner sleeve 14, as described herein.

Outer sleeve 60 is translatable relative to inner sleeve 14 between a proximal, open position, as shown in FIG. 7, and a distal, closed position, as shown in FIG. 6. In the proximal position, implant dispenser 12 is disposed in an open position such that receivers 100 are moveable within inner sleeve 14 to an ejection position within chamber 48. In the distal positon, implant dispenser 12 is disposed in a closed position such that outer sleeve 60 is engaged with tabs 50 such that tabs 50 apply force F4 to the proximal surface of receiver 100a, as described herein, such that translation of receiver 100a, in the direction shown by arrow B, is resisted and/or prevented, for example, during connection of receiver 100a with a screw shaft 150, as described herein.

An actuator 70 is connected with outer sleeve 60 at proximal end 62. Actuator 70 includes a handle 72. Handle 72 includes a surface 74 that defines a cavity 76. Outer sleeve 60 is disposed with cavity 76. Pins 78 connect handle 72 with outer sleeve 60. A spring 80 is disposed with cavity 76 and about outer sleeve 60. Pins 78 are connected with spring 80 and handle 72. In some embodiments, spring 80 comprises a compression spring such that spring 80 is biased to an expanded configuration.

Figure 9:
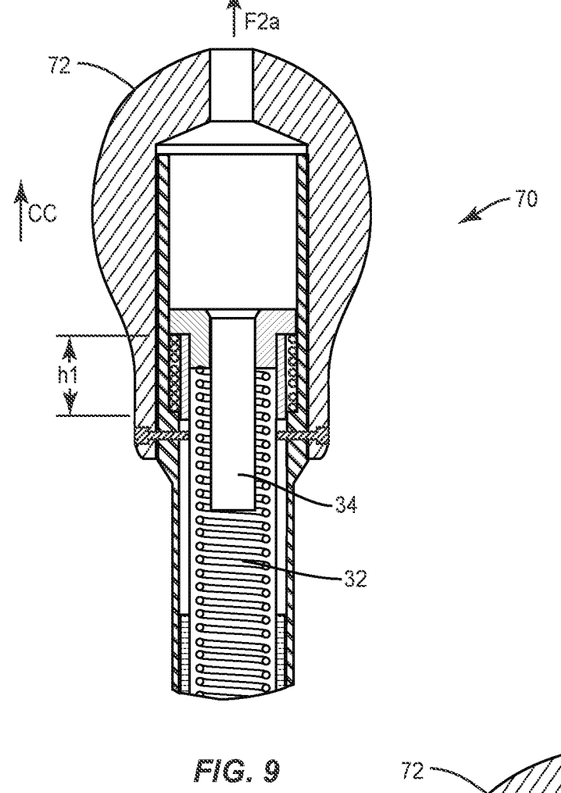
FIG. 9 is a break away view of the components shown in FIG. 5.

In some embodiments, spring 80 is fully compressed, as shown in FIG. 9, such that implant dispenser 12 is disposed in an open position. A force F2 is applied to handle 72, in a direction shown by arrow C in FIG. 10, causing translation of outer sleeve 60. As force F2 is applied to handle 72, spring 80 extends to a fully expanded orientation and a movable limit such that an inner surface of handle 72 engages a flange of spring guide 34. Spring 80 is expanded from a height h1 to a height h2, a shown in FIGS. 9 and 10. As handle 72 is engaged to expand spring 80, outer sleeve 16 translates relative to inner sleeve 14 to the distal position. Implant dispenser 12 is disposed in a closed position such that outer sleeve 60 is engaged with tabs 50 such that tabs 50 apply force F4 to the proximal surface of receiver 100a, as described herein. Upon engagement of the inner surface of handle 72 with the flange of spring guide 34, handle 72, outer sleeve 16 and inner sleeve 14 are fixed for simultaneous movement, for example, to connect receiver 100a with a screw shaft 150, as described herein.

Upon connection of receiver 100a with screw shaft 150, a force F2a is applied to handle 72, in a direction shown by arrow CC in FIG. 9, causing translation of outer sleeve 60 relative to inner sleeve 14 to the open position. As force F2a is applied to handle 72, spring 80 fully compresses from height h2 to a height h1. A force greater than force F3 is applied to implant dispenser 12 to draw collet 40 from receiver 100a such that receiver 100a is released from collet 40. In some embodiments, force F2 is approximately 6 lbs.

Receivers 100 extend along axis a when disposed with inner sleeve 14. Each receiver 100 includes a pair of spaced apart arms that define an implant cavity configured for disposal of a component of a spinal construct, such as, for example, a spinal rod (not shown). Each receiver 100 includes a surface 106 that defines a cavity 108. Cavity 108 is configured for disposal of a head 152 of a screw shaft 150, as described herein. Head 152 is engageable with surface 106 in a manually engageable configuration, as described herein, to connect receiver 100 with screw shaft 150 to comprise a bone screw. Each screw shaft 150 includes head 152 and a threaded shaft 154. Shaft 154 is configured to penetrate tissue, such as, for example, bone.

In some embodiments, implant dispenser 12 is utilized to forcibly snap-fit the components of receiver 100 and screw shaft 150 together. In some embodiments, implant dispenser 12 is utilized to forcibly pop-fit the components of receiver 100 and screw shaft 150 together. In some embodiments, a force in a range of 2-50 N is required to manually engage receiver 100 and screw shaft 150 and forcibly assemble the components. In some embodiments, a force in a range of 5-10 N is required to manually engage receiver 100 and screw shaft 150 and forcibly assemble the components.

In some embodiments, receiver 100 is connectable with screw shaft 150 to comprise various bone fastener configurations, such as, for example, a posted screw, a pedicle screw, a bolt, a bone screw for a lateral plate, an interbody screw, a uni-axial screw, a fixed angle screw, a multi-axial screw, a side loading screw, a sagittal adjusting screw, a transverse sagittal adjusting screw, an awl tip, a dual rod multi-axial screw, midline lumbar fusion screw and/or a sacral bone screw.

In some embodiments, spinal implant system 10 may comprise the use of microsurgical and image guided technologies, such as, for example, surgical navigation components employing emitters and sensors, which may be employed to track introduction and/or delivery of implant dispenser 12 and/or implants disposed therewith to a surgical site. See, for example, the surgical navigation components and their use as described in U.S. Pat. Nos. 6,021,343, 6,725,080, 6,796,988, the entire contents of each of these references being incorporated by reference herein.

Figure 11:
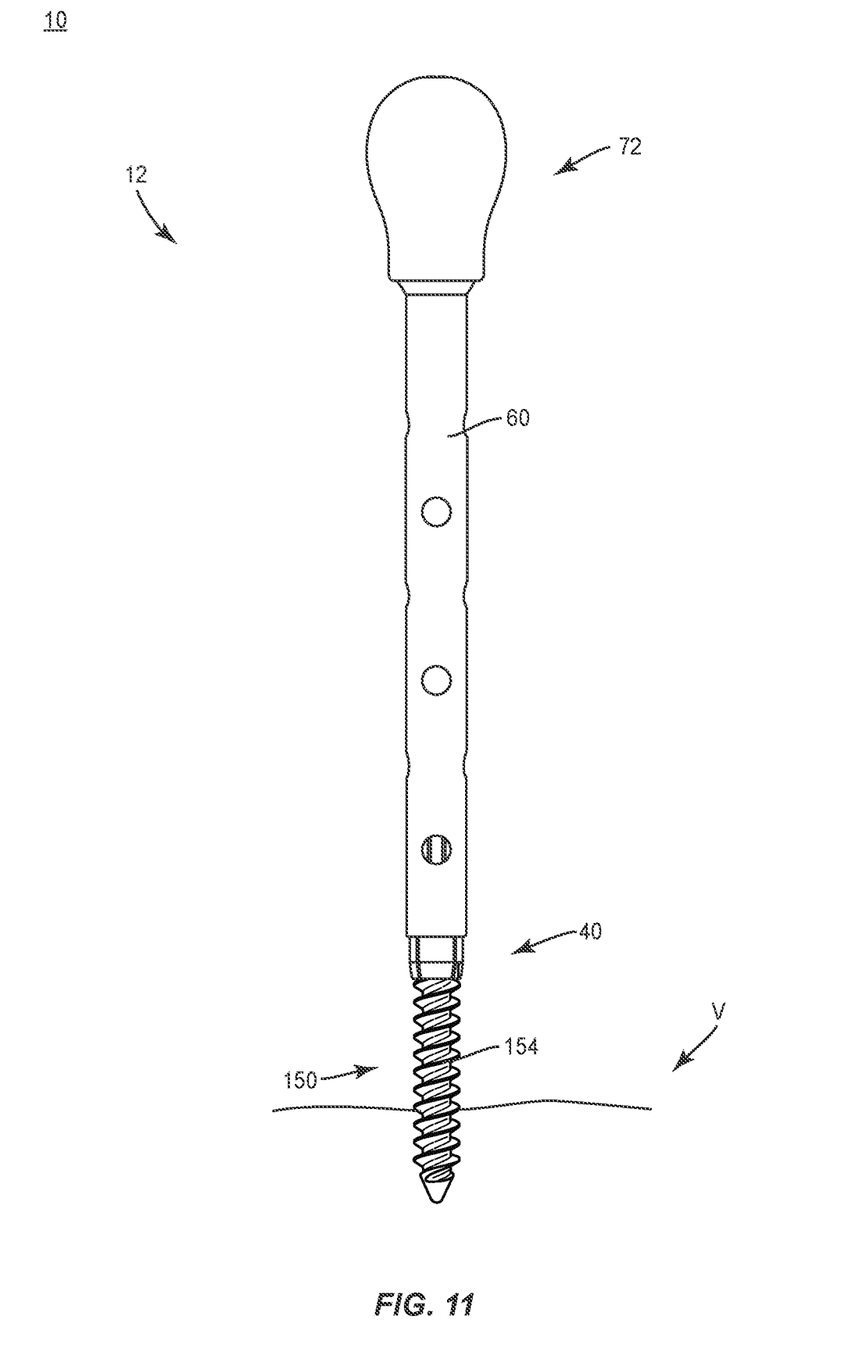
FIG. 11 is a side view of components of one embodiment of a surgical system in accordance with the principles of the present disclosure disposed with vertebrae.
Figure 12:
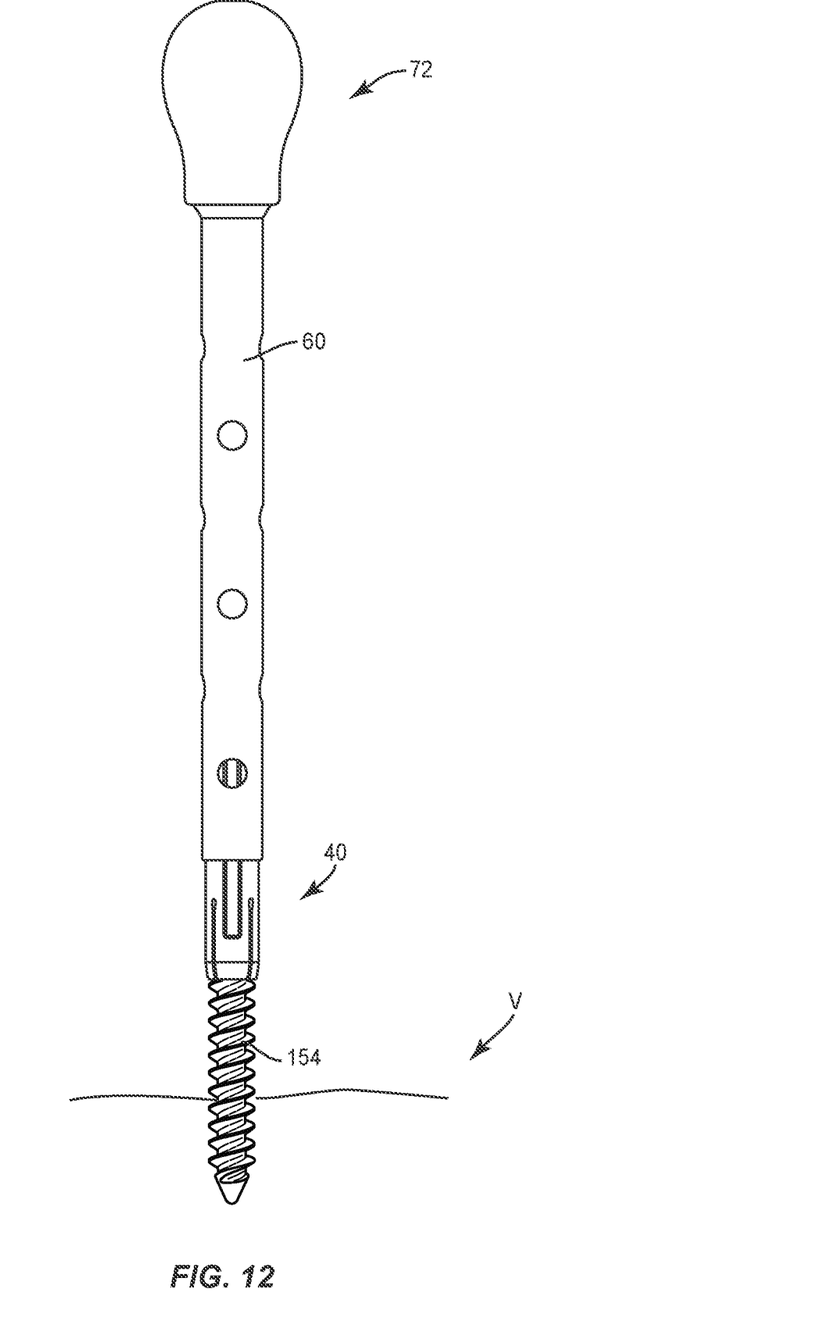
FIG. 12 is a side view of the components and vertebrae shown in FIG. 11.
Figure 13:
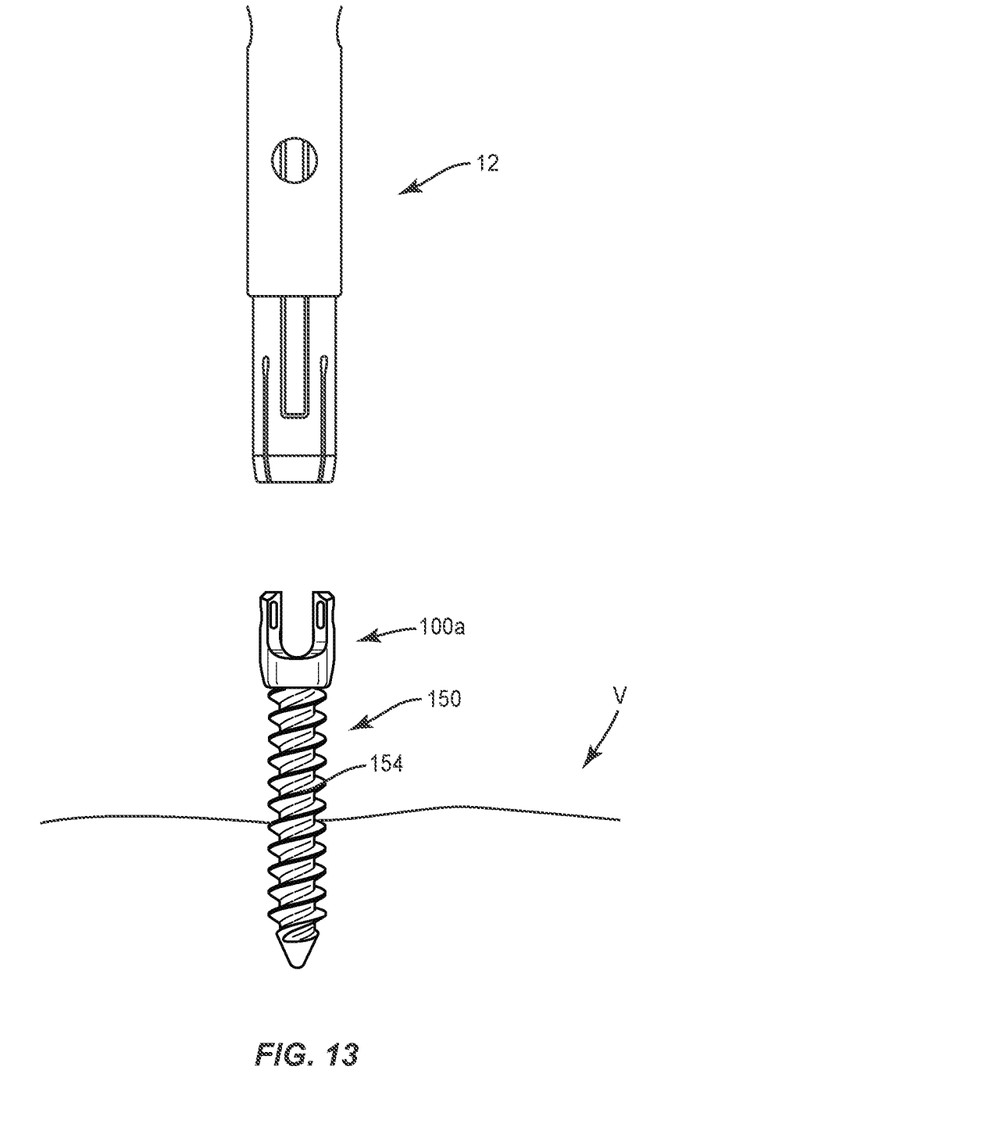
FIG. 13 is a side view of the components and vertebrae shown in FIG. 11.

In assembly, operation and use, spinal implant system 10, similar to the systems and methods described herein, includes implant dispenser 12 and/or implants disposed therewith, and is employed with a surgical procedure for treatment of a spinal disorder affecting a section of a spine of a patient, as discussed herein. The components of spinal implant system 10 are employed with a surgical procedure for treatment of a condition or injury of an affected section of the spine, such as, for example, vertebrae V, as shown in FIGS. 11-13.

In use, to treat a selected section of vertebrae V, a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V as well as for aspiration and irrigation of a surgical region.

Figure 1:
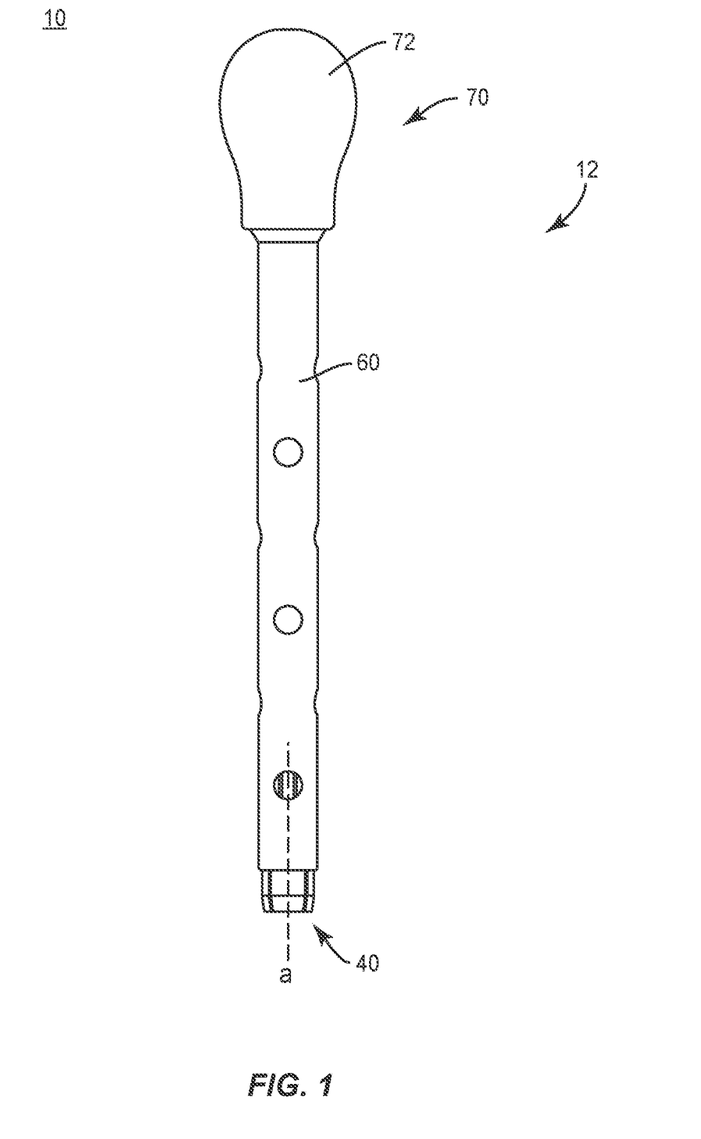
FIG. 1 is a side view of components of one embodiment of a surgical system in accordance with the principles of the present disclosure.
Figure 2:
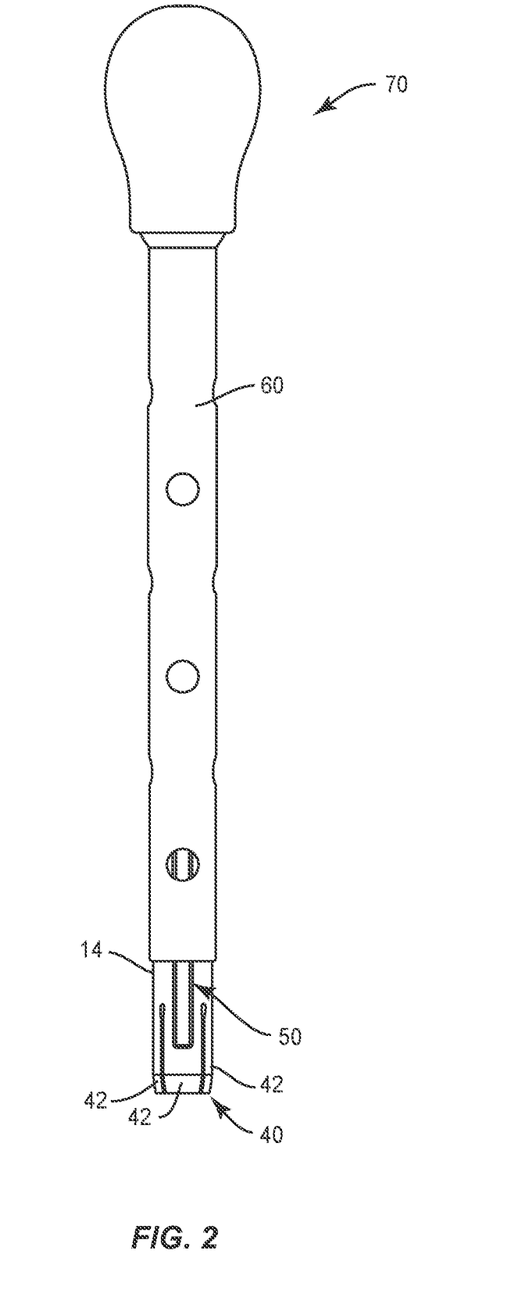
FIG. 2 is a side view of the components shown in FIG. 1.
Figure 3:
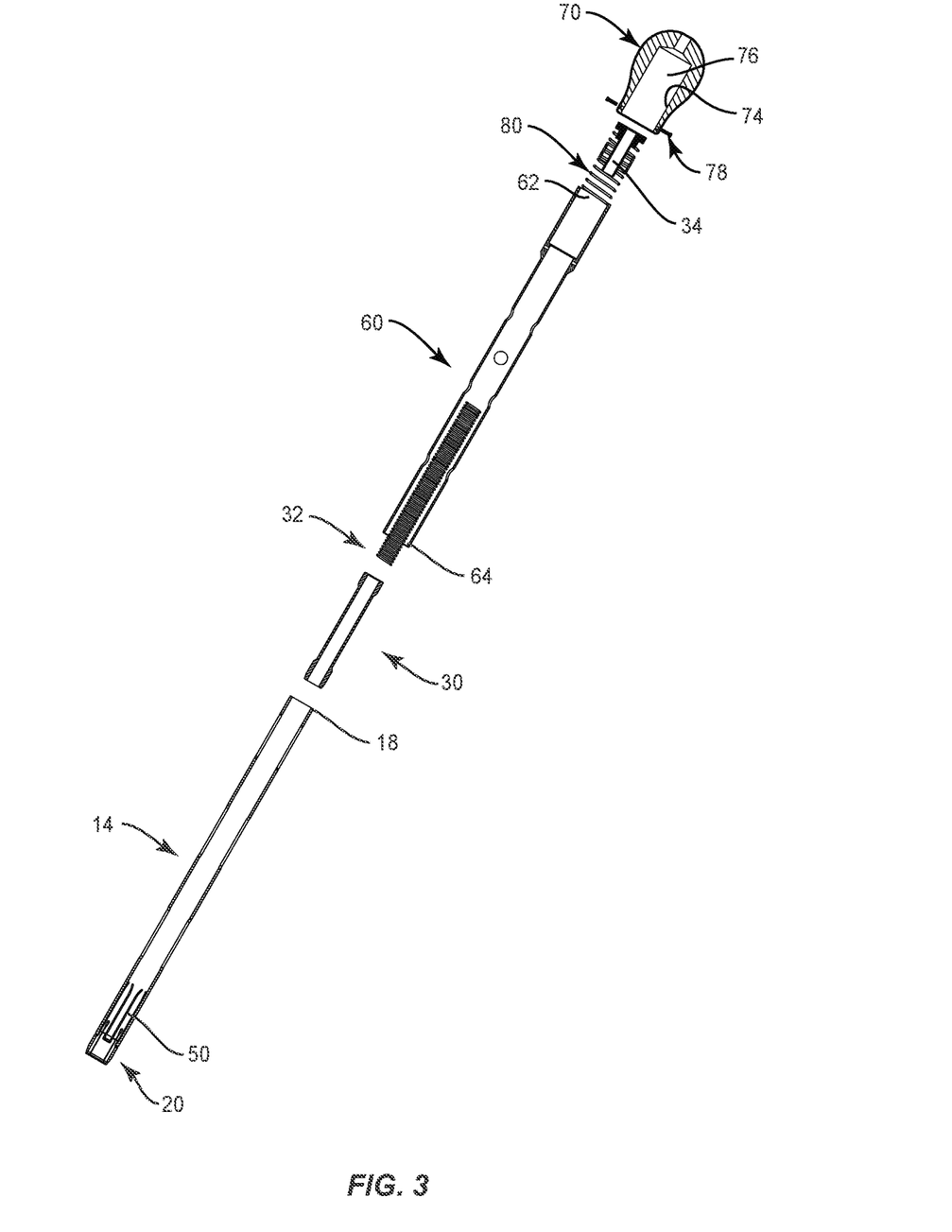
FIG. 3 is a side cross section view of the components shown in FIG. 1 with parts separated.
Figure 4:
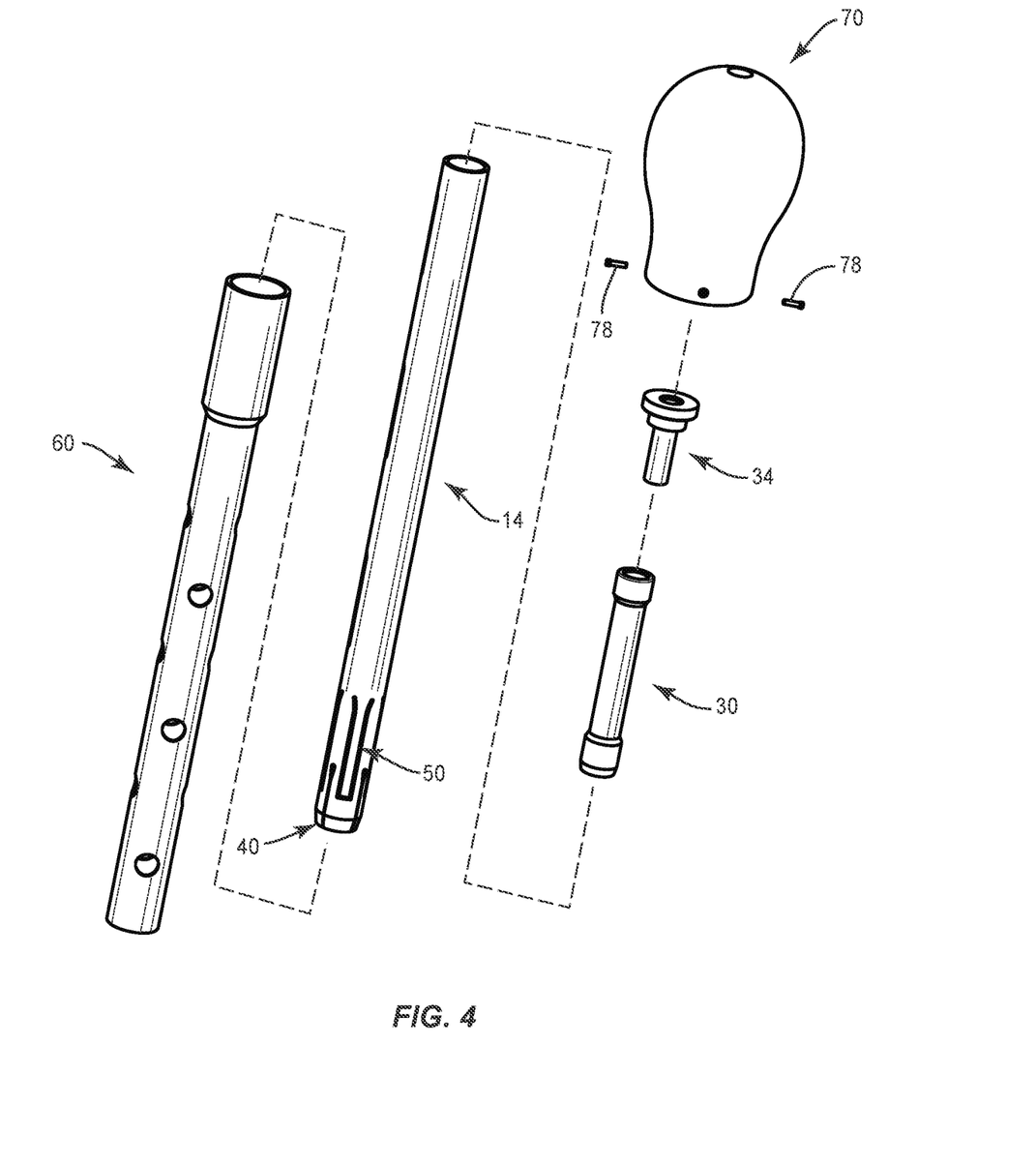
FIG. 4 is a perspective view of the components shown in FIG. 1 with parts separated.

Pilot holes (not shown) are made in selected levels of vertebrae V for receiving one or more screw shafts 150. Spring 80 is fully compressed, as shown in FIG. 9, such that implant dispenser 12 is disposed in the proximal, open position, as shown in FIG. 2. Receivers 100 are stacked in a serial orientation within cavity 24 to facilitate loading, storage and/or ejection of receivers 100 from implant dispenser 12. Spring 32 applies a force F1, as shown in FIG. 8, to piston 30 to urge receivers 100 into distal portion 18 of inner sleeve 14 such that receiver 100a is disposed in the ejection position in collet 40. Force F1 of spring 32 overcomes force F4 applied to the distal surface of the next proximally disposed receiver 100 to deflect tabs 50 outwardly to facilitate loading of the next receiver 100 into collet 40. Fingers 42 of collet 40 apply a force F3 to receiver 100a to retain receiver 100a within chamber 48.

Figure 10:
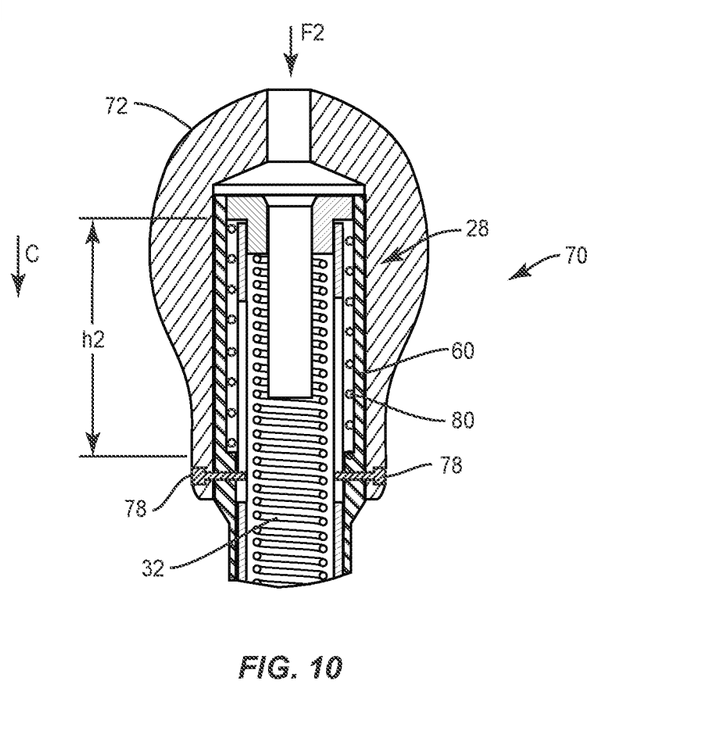
FIG. 10 is a break away view of the components shown in FIG. 5.

Force F2 is applied to handle 72 and spring 80 extends to a fully expanded orientation, as shown in FIG. 10. As handle 72 is engaged to expand spring 80, outer sleeve 16 translates relative to inner sleeve 14 to the distal, closed position, as shown in FIG. 11. Implant dispenser 12 is disposed in a closed position such that outer sleeve 60 is engaged with tabs 50 and tabs 50 apply force F4 to the proximal surface of receiver 100a to resist and/or prevent axial translation of receiver 100a back into inner sleeve 14, as described herein.

Implant dispenser 12 is oriented such that cavity 108 of ejection receiver 100a is aligned with head 152 of screw shaft 150. Force F3 is greater than force F1 to retain receivers 100 with implant dispenser 12 and prevent spring 32 from undesirably driving and/or releasing receivers 100.

Head 152 is engageable with surface 106 in a manually engageable configuration, as described herein, to connect receiver 100 with screw shaft 150 to comprise a bone screw.

Force F2a is applied to handle 72, as shown in FIG. 9, causing translation of outer sleeve 60 relative to inner sleeve 14 to the open position, as shown in FIG. 12. As force F2a is applied to handle 72, spring 80 fully compresses. Force F3 is overcome by drawing collet 40 off of receiver 100a connected with screw shaft 150, which is attached with vertebrae V, with a force greater than force F3. Receiver 100a is released from collet 40 and engaged with screw shaft 150, as shown in FIG. 13. A next receiver 100 translates into chamber 48 into the ejection position, as described herein, for connection with a second screw shaft 150.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
    a first member extending along a longitudinal axis between a proximal end and an opposite distal end, the first member including a wall defining a cavity extending along the longitudinal axis and configured for disposal of a bone fastener receiver, the first member including a collet within the cavity, the collet retaining the receiver with the first member, the first member including a piston engageable with the receiver in a first, release, direction along the longitudinal axis, the wall defining a tab;
    a second member movable relative to the first member between a first position and a second position such that the second member engages the tab in the second position to prevent movement of the receiver in an opposite second direction along the longitudinal axis; and
    an actuator including a handle and a spring, an end of the second member being positioned within the handle such that the spring is positioned about the second member to bias the second member to the second position,
    wherein the second member includes an outer sleeve and the first member includes an inner sleeve disposed within the outer sleeve.

2. A surgical instrument as recited in claim 1, wherein the receiver is movable within the first member when the second member is in the first position.

3. A surgical instrument as recited in claim 1, wherein the receiver comprises a plurality of receivers disposed in a stacked orientation within the cavity.

4. A surgical instrument as recited in claim 1, wherein the collet is expandable to eject the receiver in the first direction.

5. A surgical instrument as recited in claim 1, wherein the collet has an expandable surface engageable with the receiver to retain the receiver with the first member.

6. A surgical instrument as recited in claim 1, wherein the collet defines a chamber configured for disposal of the receiver.

7. A surgical instrument as recited in claim 1, wherein the tab is biased outwardly from the first member.

8. A surgical instrument as recited in claim 1, wherein the tab includes a pair of spring biased tabs.

9. A surgical instrument as recited in claim 1, wherein the piston applies a first force to urge the receiver in the first direction and the collet applies a second force to the receiver.

10. A surgical instrument as recited in claim 1, wherein the receiver is attachable with a screw shaft engaged with vertebral tissue.

11. A surgical instrument as recited in claim 1, wherein the tab includes a cantilever arm disposed in alignment with the wall.

12. A surgical instrument as recited in claim 1, wherein the piston applies a first force to urge the receiver in the first direction and the collet applies a second force to the receiver, the first force overcoming the second force to permit ejection of the receiver.

13. A surgical instrument as recited in claim 1, wherein the end of the second member and a portion of the spring are positioned within a cavity of the handle.

14. A surgical instrument comprising:
    a first member extending along a longitudinal axis between a proximal end and an opposite distal end, the first member including a wall defining a cavity extending along the longitudinal axis and configured for disposal of a plurality of bone fastener receivers, the first member including a an expandable collet positioned within the cavity that retains the receivers with the first member, the receivers being disposed in a stacked orientation within the cavity, the first member including a piston engageable with the receivers in a first, release, direction along the longitudinal axis, the wall defining a pair of spring biased tabs;
    a second member movable relative to the first member between a proximal position and a distal position such that the second member engages the tabs in the distal position to prevent movement of the receivers in an opposite second direction along the longitudinal axis; and an actuator including a handle and a spring, an end of the second member being positioned within the handle such that the spring is positioned about the second member to bias the second member toward the distal position.

15. A surgical instrument as recited in claim 14, wherein the actuator is configured to translate the second member relative to the first member such that the actuator engages the first member when the second member is in the distal position.

16. A surgical instrument as recited in claim 14, wherein the tabs each include a cantilever arm disposed in alignment with a wall of the first member.

17. A surgical instrument comprising:

an inner tubular sleeve extending along a longitudinal axis between a proximal end and an opposite distal end, the inner sleeve including a wall defining a cavity extending along the longitudinal axis and configured for disposal of a plurality of bone fastener receivers, the inner sleeve including an expandable collet within the cavity, the inner sleeve further including a piston engageable with the receivers in a first, release, direction along the longitudinal axis, the wall defining at least one tab;

an outer tubular sleeve movable relative to the inner sleeve between a proximal position and a distal position such that the outer sleeve engages the at least one tab in the distal position to prevent movement of at least one receiver in an opposite second direction along the longitudinal axis; and an actuator including a handle and a spring, an end of the outer sleeve being positioned within the handle such that the spring is positioned about the outer sleeve to bias the outer sleeve toward the distal position.

18. A surgical instrument as recited in claim 17, wherein the receivers are disposed in a stacked orientation within the cavity.

19. A surgical instrument as recited in claim 17, wherein the actuator engages the inner sleeve.

20. A surgical instrument as recited in claim 17, wherein the piston applies a first force to urge the receivers in the first direction and the collet applies a second force to the receivers, the second force being greater than the first force.

* * * * *